(12) United States Patent
Lin et al.

(10) Patent No.: US 9,075,865 B2
(45) Date of Patent: *Jul. 7, 2015

(54) SYSTEM FOR ESTIMATING AGE OF A USER BASED ON MASS DATA

(71) Applicant: TENCENT TECHNOLOGY (SHENZHEN) COMPANY LIMITED, Shenzhen (CN)

(72) Inventors: Lebin Lin, Shenzhen (CN); Chuan Chen, Shenzhen (CN); Guohui Ling, Shenzhen (CN); Ali Sun, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/501,116

(22) Filed: Sep. 30, 2014

(65) Prior Publication Data

US 2015/0019570 A1    Jan. 15, 2015

Related U.S. Application Data

(63) Continuation of application No. 13/380,326, filed as application No. PCT/CN2010/074318 on Jun. 23, 2010, now Pat. No. 8,909,638.

(30) Foreign Application Priority Data

Aug. 21, 2009    (CN) .......................... 2009 1 0042053

(51) Int. Cl.
| | | |
|---|---|---|
| *G06F 7/00* | (2006.01) | |
| *G06F 17/30* | (2006.01) | |
| *G06F 19/00* | (2011.01) | |
| *H04L 12/58* | (2006.01) | |
| *H04L 29/06* | (2006.01) | |

(52) U.S. Cl.
CPC ........ *G06F 17/30616* (2013.01); *G06F 19/327* (2013.01); *G06F 19/3443* (2013.01); *H04L 51/32* (2013.01); *H04L 65/403* (2013.01)

(58) Field of Classification Search
None
See application file for complete search history.

(56) References Cited

U.S. PATENT DOCUMENTS

| | | | | |
|---|---|---|---|---|
| 5,763,837 | A * | 6/1998 | Davignon et al. | 174/113 R |
| 7,912,246 | B1 * | 3/2011 | Moon et al. | 382/103 |
| 2005/0106550 | A1 * | 5/2005 | Hayashi et al. | 434/362 |

(Continued)

FOREIGN PATENT DOCUMENTS

| | | |
|---|---|---|
| CN | 101635009 A | 1/2007 |
| JP | 2004-318632 A | 11/2004 |
| JP | 2006-119920 A | 5/2006 |

(Continued)

OTHER PUBLICATIONS

International Search Report for Application No. PCT/CN2010/074318 dated Oct. 21, 2010, and its English translation thereof.

*Primary Examiner* — Debbie Le
*Assistant Examiner* — Hasanul Mobin
(74) *Attorney, Agent, or Firm* — Harness, Dickey & Pierce, P.L.C.

(57) ABSTRACT

An initial weight is configured for each kind of basic age data, an age weight of the user in different basic age data is obtained according to the initial weight and age similarity of the user in different kinds of basic age data, and the age with the largest age weight is determined as the age of the user.

11 Claims, 3 Drawing Sheets

(56) References Cited

U.S. PATENT DOCUMENTS

2010/0082360 A1* 4/2010 Chien et al. ................ 705/1
2012/0051629 A1* 3/2012 Ueki et al. .................. 382/159

FOREIGN PATENT DOCUMENTS

| JP | 2006119920 A | * | 5/2006 |
| JP | 2007-164439 A | | 6/2007 |

* cited by examiner

SYSTEM FOR ESTIMATING AGE OF A USER BASED ON MASS DATA

CROSS-REFERENCE TO RELATED APPLICATIONS

This application is a continuation of U.S. patent application Ser. No. 13/380,326, filed on Dec. 22, 2011. This application claims the benefit and priority of Chinese Application No. 200910042053.9, filed Aug. 21, 2009. The entire disclosures of the above applications are incorporated herein by reference.

FIELD

The present disclosure relates to mass data processing techniques, and more particularly, to a system for determining age of a user based on mass data.

BACKGROUND

This section provides background information related to the present disclosure which is not necessarily prior art.

With popularization of the Internet, network has become one indispensable part of people's daily lives. The Internet may provide various kinds of services to users, e.g. e-shopping, acquiring information, and entertainment. Age is a basic attribute of a user. With respect to users of different ages, different customized Internet services may be provided. However, the uses generally do not provide their real ages on the Internet. Therefore, determining the real age of a user accurately has become a problem.

One existing method obtains age data provided by the user and estimates the age of the user through simple boundary value filtering. Specifically, an age range of the user is estimated according to experiences, and values outside of the age range are filtered. Thus, the age of the users are estimated. However, this method relies heavily on the ages provided by the users and, thus, it is inaccurate.

SUMMARY

This section provides a general summary of the disclosure, and is not a comprehensive disclosure of its full scope or all of its features.

According to various embodiments of the present disclosure, a system for estimating age of a user based on mass data includes the following:
memory;
one or more processors; and
at least one unit stored in the memory for execution by the one or more processors, which comprises at least one of the following:
a weight configuring unit to obtain different kinds of basic age data of the user from network products that comprise an instant messaging tool and a Social Networking Service (SNS), wherein the different kinds of basic age data are provided by the user by filling in ages through the different kinds of network products, obtain reference age data of the user through network questionnaire, compare the basic age data with the reference age data to obtain an accuracy ratio of the basic age data; and configure an initial weight for the basic age data according to the accuracy ratio;
a weight processing unit to obtain an age weight of the user in each kind of basic age data according to a sum of the initial weight and an age weight score of the kind of basic age data; wherein the age weight score of the kind of basic age data is configured according to the initial weight of the kind of the basic age data and an age similarity of the user in the different kinds of basic age data; and
an age estimating unit to search the different kinds of basic age data for the basic age data with a largest age weight, and estimate the age of the user according to the basic age data with the largest age weight;
wherein the accuracy ratio of the basic age data comprises searching the basic age data for a selected group of users whose ages conform to the reference age data, dividing the number of the users searched out by the total number of users in the basic age data, and determining the divided result as the accuracy ratio of the basic age data.

According to various embodiments of the present disclosure, a non-transitory computer readable storage medium storing one or more programs for estimating age of a user based on mass data is provided; the set of instructions is to direct at least one processor to perform the following acts:
obtaining different kinds of basic age data of the user from network products that include an instant messaging tool and a Social Networking Service (SNS), wherein the different kinds of basic age data are provided by the user by filling in ages through the different kinds of network products, configuring an initial weight for each kind of basic age data according to an accuracy ratio of the basic age data;
obtaining an age weight of the user in each kind of basic age data according to a sum of the initial weight and an age weight score of the kind of basic age data; wherein the age weight score of the kind of basic age data is configured according to the initial weight of the kind of basic age data and an age similarity of the user in different kinds of basic age data; and
searching the different kinds of basic age data for the basic age data with the largest age weight, estimating the age of the user according to the basic age data with the largest age weight;
wherein the configuring the initial weight for each kind of basic age data comprises the following:
obtaining reference age data of the user through a network inquiry,
comparing the basic age data with the reference age data to obtain an accuracy ratio of the basic age data; and
configuring the initial weight for the basic age data according to the accuracy ratio; and
wherein the accuracy ratio of the basic age data comprises searching the basic age data for a selected group of users whose ages conform to the reference age data, dividing the number of the users searched out by the total number of users in the basic age data, and determining the divided result as the accuracy ratio of the basic age data.

According to the method and system for determining the age of the user provided by the various embodiments of the present disclosure, an initial weight is configured for the basic age data, an age weight of the user in different basic age data is obtained according to the initial weight and age similarity of the user in different kinds of basic age data, and the age with the largest age weight is determined as the age of the user. Since the multiple kinds of basic age data provided by the user are evaluated in combination, the age with the largest age weight is closer to real age of the user. Therefore, the accuracy of determining the age of the user is increased.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Reference throughout this specification to "one embodiment," "an embodiment," "specific embodiment," or the like in the singular or plural means that one or more particular features, structures, or characteristics described in connection with an embodiment is included in at least one embodiment of the present disclosure. Thus, the appearances of the phrases "in one embodiment" or "in an embodiment," "in a specific embodiment," or the like in the singular or plural in various places throughout this specification are not necessarily all referring to the same embodiment. Furthermore, the particular features, structures, or characteristics may be combined in any suitable manner in one or more embodiments.

Figure 1:
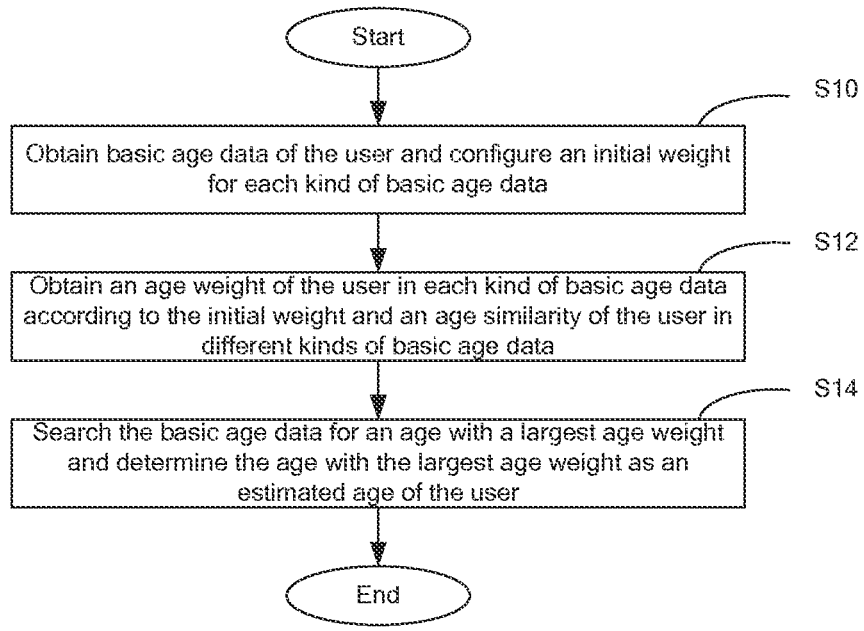
FIG. 1 is a flowchart illustrating a method for determining age of a user based on mass data according to various embodiments of the present disclosure.

FIG. 1 is a flowchart illustrating a method for determining age of a user based on mass data. The method includes the following:

S10: basic age data of the user is obtained and an initial weight is configured for each kind of basic age data, wherein the basic age data is provided by the user when filing information through various kinds of network products, e.g. instant messaging tool or Social Networking Service (SNS), etc.

Figure 2:
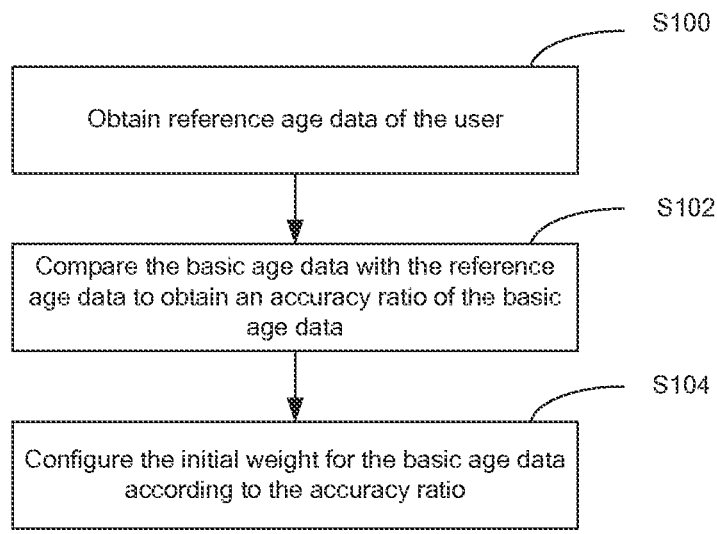
FIG. 2 is a flowchart illustrating a method for configuring an initial weight for the basic age data according to various embodiments of the present disclosure.

As shown in FIG. 2, the method for configuring the initial weight for the basic age data is as follows.

S100: reference age data of the user is obtained.

The reference age data of the user may be obtained through a network questionnaire. Since questions configured by the network questionnaire are relatively precise, the age obtained through the network questionnaire is more accurate than that directly filled in by the user.

S102: the basic age data is compared with the reference age data and an accuracy ratio of the basic age data is obtained.

Search each kind of basic age data for users whose ages conform to corresponding reference ages in the reference age data and divide the number of the users searched out by a total number of users in the user group to obtain the accuracy ratio of the basic age data.

In particular, with respect to each kind of basic age data, search a user group corresponding to the basic age data to obtain the number of users whose basic ages conform to their reference ages in the reference age data. Then determine the proportion between this number and the total number of users in the user group corresponding to the basic age data as an accuracy ratio of the kind of basic user data. The term "conform" means that the basic age and the reference age are the same, or that the difference between them is within a certain range, e.g. 3 years.

Basic age data obtained through various ways belongs to different kinds of age data. For example, basic age data obtained through an instant messaging tool belongs to one kind of basic age data and basic age data obtained through SNS belongs to another kind of basic age data.

S104: configure an initial weight for the basic age data according to the accuracy ratio.

In various embodiments, the accuracy ratio of the basic age data has three levels: low, medium and high. Corresponding to the accuracy ratio in the three levels, initial weights configured for the basic age data are respectively P1, P2, and P3. For example, P1=1, P2=5, and P3=9. Suppose that basic age data IM1, IM2, ..., IMn of n users are obtained through the instant messaging tool; basic age data SNS1, SNS2, ..., SNSn of the n users are obtained through SNS, and reference age data R1, R2, ..., Rn of the n users are obtained by questionnaire. Through comparing IM1, IM2, ..., IMn with R1, R2, ..., Rn, it is possible to obtain the accuracy ratio of the basic age data obtained by the instant messaging tool. Suppose this accuracy ratio is low. One would then configure the initial weight of the basic age data obtained by the instant messaging tool as P1. Similarly, the accuracy ratio of the basic age data obtained by the SNS can be obtained. Suppose this accuracy ratio is medium. Then the initial weight configured for the basic age data obtained by the SNS is P2.

In various embodiments, it is also possible to configure initial weights for different kinds of basic age data according to sources of the basic age data. For example, age data obtained from registration information of a network service such as alumni record is more accurate. Therefore, the initial weight configured for this kind of basic age data may be relatively higher than others.

S12: obtain an age weight of the user in each kind of basic age data according to the initial weight of the basic age data and an age similarity of the user in different kinds of basic age data.

Figure 3:
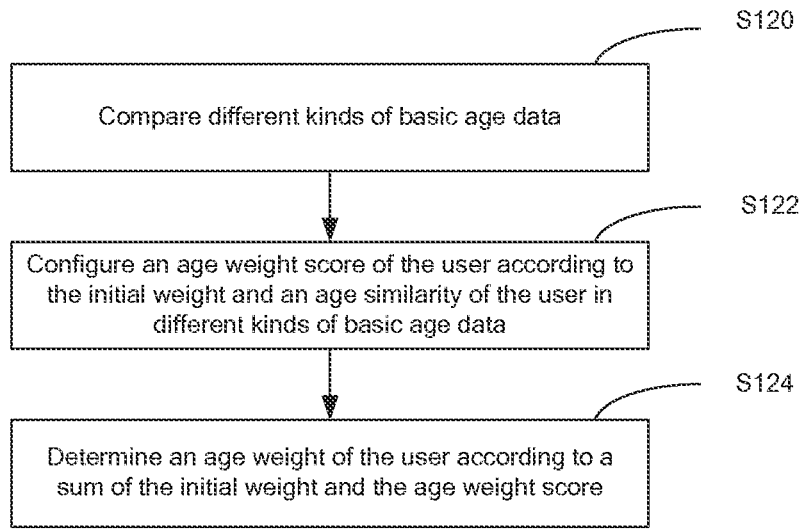
FIG. 3 is a flowchart illustrating a method for obtaining age weights of the user and different kinds of basic age data according to various embodiments of the present disclosure.

As shown in FIG. 3, the method for obtaining age weights of the user in different kinds of basic age data is as follows.

S120: compare different kinds of basic age data. Specifically, with respect to multiple kinds of basic age data obtained through various methods, compare ages of the user in the different kinds of basic age data.

S122: configure an age weight score for the user according to the initial weights of different kinds of basic age data and an age similarity of the user in different kinds of basic age data. In various examples, the age similarity of the user in different kinds of basic age data may be: same age, similar ages, and different ages, wherein the age similarity of similar ages means that the difference between the ages is within 3 years, and the age similarity of different ages means that the difference between the ages is larger than 3 years. Compare the initial weights of different kinds of basic age data to obtain a weight relationship between the basic age data. The weight relationship may be: same weight, similar weights, and different weights, wherein the weight relationship of same weight means that the two kinds of basic age data have the same weight level (i.e. both of them are high, medium, or low); the weight relationship of similar weights means that weights of the two kinds of basic age data have a difference of one level (i.e. the two weight levels are high and medium or medium and low); the weight relationship of different weights means that the weights of the two kinds of basic age data have a difference of two levels (i.e. the weights are high and low). In one example, age weight scores of the user are configured as shown in Table 1.

TABLE 1

| Weight relationship | Age similarity | | |
|---|---|---|---|
| | Same age | similar ages | Different ages |
| Same weight | +A1 | +A4 | 0 |
| Similar weights | +A2 | +A5 | 0 |
| Different weights | +A3 | +A6 | 0 |

For example, A1=1, A2=2, A3=3, A4=4, A5=5, and A6=6.

S124: determine an age weight of the user according to a sum of the initial weight and the age weight score. In the above example, compare different kinds of basic age data. As to each kind of basic age data, obtain a weight relationship between it and each other kind of basic age data and an age similarity of the user under the weight relationship. The age weight score of the user and the basic age data is the sum of all age weight scores obtained by comparing the basic age data with other basic age data.

In one example, three kinds of basic age data of the user are M, N, and O. In this example, suppose the initial weights of the three kinds of basic age data are respectively P1, P2, and P3. With respect to three users a, b, and c, suppose the ages of the three users in the basic age data M are respectively Ma, Mb, and Mc, the ages of the three users in the basic age data N are respectively Na, Nb, and Nc, and the ages of the three users in the basic age data O are respectively Oa, Ob, and Oc. Compare the basic age data M, N, and O. Suppose the weights of the basic age data M and the basic age data N are similar, the weights of the basic age data M and the basic age data O are different, and the weights of the basic age data N and the basic age data O are similar. With respect to user a, suppose Ma=25, Na=25, and Oa=23, i.e. Ma and Na have the same age, Ma and Oa have similar ages, and Na and Oa have similar ages. According to the age weight scores configured in Table 1, it is ascertained that the age weight of Ma is P1+A2+A6, the age weight of Na is P2+A2+A5, and the age weight of Oa is P3+A6+A5. Similarly, the age weights of user b and user c may be obtained following the above method.

S14: search different kinds of basic age data for an age with the largest age weight and determine the age with the largest age weight as an estimated age of the user. In the above example, as to user a, determine the age with the largest age weight among Ma, Na, and Oa as the estimated age of user a. Since the age with the largest age weight is closer to the real age of the user, the age is determined more accurately.

In various embodiments, after obtaining the estimated age of the user, compare the age weight of the estimated age and initial weight. Classify the age weight of the estimated age of the user into one of three levels: high weight, medium weight, and low weight. In one example, suppose the initial weights of three kinds of basic age data are P1, P2, and P3. If the age weight of the estimated age is smaller than or equal to P2, the age weight is low. If the age weight of the estimated age is larger than P2 but is smaller than or equal to P3, the age weight is medium. If the weight of the estimated age is larger than P3, the age weight is high.

Figure 4:
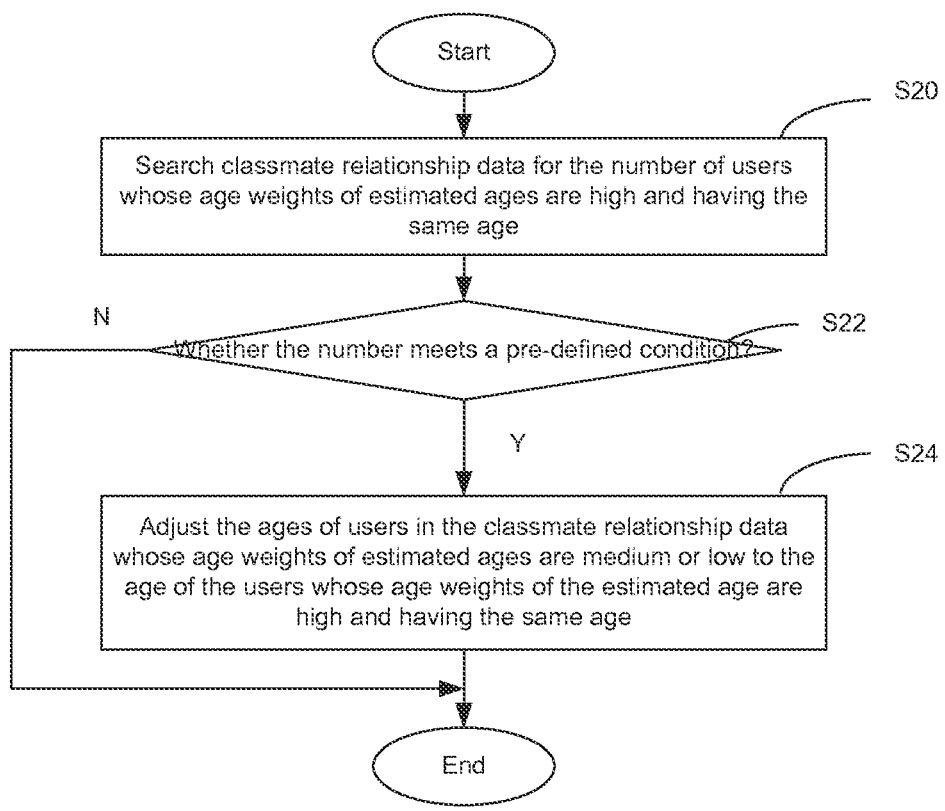
FIG. 4 is a flowchart illustrating a method for determining the age of the user according to classmate relationship data according to various embodiments of the present disclosure.

FIG. 4 is a flowchart of a method for determining age of a user according to classmate relationship data. The method includes the following steps.

S20: search classmate relationship data for the number of users whose age weights of estimated ages are high and have the same estimated age. The classmate relationship data is a collection of data for users having a classmate relationship. Users having a classmate relationship are usually the same or similar ages. The classmate relationship data may be obtained from classmate group members and a friend group of the user.

S22: determine whether the number meets a pre-defined condition. If the number meets the pre-defined condition, proceed to step S24; otherwise, the procedure ends. In various embodiments, the pre-defined condition is: m>3 and m/n>=1/4, wherein m denotes the number of users whose age weights of the estimated ages are high and having the same estimated age, n denotes a total number of users in the classmate relationship.

S24: adjust estimated ages of uses whose age weights of the estimated ages are medium or low in the classmate relationship to be the estimated age of the users whose age weights of the estimated age are high and having the same estimated age. In various embodiments, if the number of users whose age weights of the estimated age are high and having the same estimated age meets the above pre-defined condition, since the estimated ages of these users are more accurate and ages of users in a classmate relationship are usually the same or similar, the ages of the users whose age weights are low or medium are adjusted according to the estimated age of the users whose age weights are high. Thus, the estimated ages are more accurate.

Figure 5:
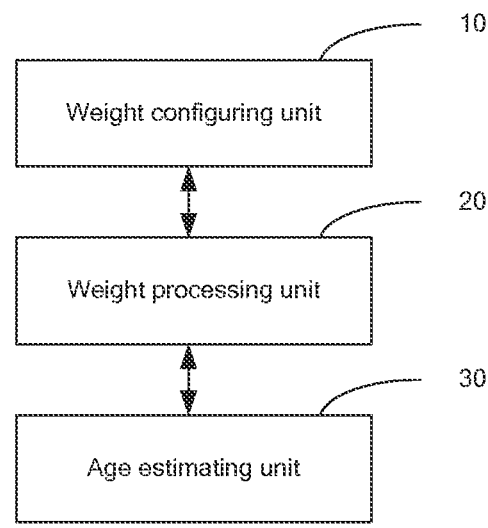
FIG. 5 is a diagram illustrating a structure of a system for determining the age of a user based on mass data according to various embodiments of the present disclosure.

FIG. 5 is a diagram illustrating a structure of a system for determining age of a user based on mass data. As shown in FIG. 5, the system includes: a weight configuring unit 10, a weight processing unit 20 and an age estimating unit 30.

The weight configuring unit 10 is to obtain basic age data of the user and configure an initial weight for each kind of basic age data.

The weight processing unit 20 is communicatively connected with the weight configuring unit 10 to obtain an age weight of the user and each kind of basic age data according to the initial weight and an age similarity of the user in different kinds of basic age data.

The age estimating unit 30 is communicatively connected with the weight processing unit 20 to search the basic age data for an age with a largest age weight and determine the age with the largest age weight as the estimated age of the user.

Figure 6:
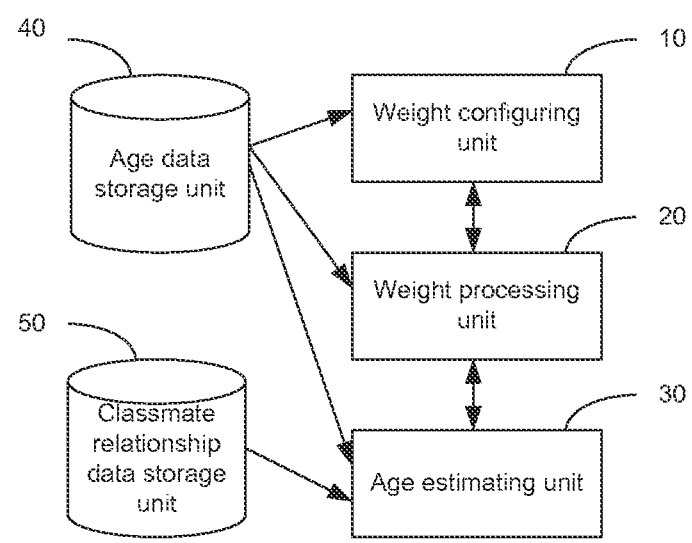
FIG. 6 is a diagram illustrating a structure of a system for determining the age of a user based on mass data according to various embodiments of the present disclosure.

FIG. 6 is a diagram illustrating another structure of a system for estimating age of a user based on mass data. As shown in FIG. 6, besides the weight configuring unit 10, the weight processing unit 20, and the age estimating unit 30, the system further includes an age data storage unit 40 and a classmate relationship data storage unit 50.

The age data storage unit 40 is communicatively connected with the weight configuring unit 10, the weight processing unit 20, and the age estimating unit 30 to store the basic age data and reference age data. The basic age data is provided by the user through various kinds of network products. The reference age data is obtained through a network questionnaire. Since questions configured by the questionnaire are relatively precise, the reference age data is more accurate than the basic age data.

The classmate relationship data storage unit 50 is communicatively connected with the age estimating unit 30 to store the classmate relationship data. Users having a classmate relationship usually have the same or similar ages. It is possible to obtain the classmate relationship data from classmate group members or a friend group of the user.

In various embodiments, the weight configuring unit 10 is further to obtain the reference age data of the user, compare the basic age data with the reference age data, obtain an accuracy ratio of the basic age data, and configure the initial weight for the basic age data according to accuracy ratio. It is possible to search each kind of basic age data to find users whose basic ages conform to the reference ages. The accuracy ratio is obtained by dividing the number of users whose basic ages conform to the reference ages by the total number of users. The weight configuring unit 10 is further to classify the accuracy ratio into three levels: high, medium, and low and configure the initial weight of the basic age data according to different levels of accuracy ratios.

In various embodiments, the weight processing unit 20 is further to compare the basic age data and configure an age weight score of the user according to the initial weight and an age similarity of the user in different kinds of basic age data. The age weight of the user is the sum of the initial weight and the age weight score. The weight processing unit 20 compares different kinds of basic age data. Each kind of basic age data obtains a weight relationship between it and another basic age data and an age similarity of the user under the weight relationship. The age weight score of the user in the basic age data is the sum of all the age weight scores obtained by comparing the basic age data and other basic age data. After the weight processing unit 20 calculates the age weight, the age estimating unit 30 searches for an age with the largest age weight and determines the age with the largest age weight as the estimated age of the user.

In various embodiments, after the age estimating unit 30 determines the estimated age of the user, the weight processing unit 20 compares the age weight of the estimated age and the initial weight and classifies them into three levels according to the determined result and the age weight of the estimated age: high weight, medium weight, and low weight.

In various embodiments, the age estimating unit 30 is further utilized to search the classmate relationship data for users whose age weights of the estimated age are high and the same age and determine whether the number of the users searched out meets a pre-defined condition. If so, modify the age of the users in the classmate relationship whose age weights are medium or low to be the estimated age of the users whose age weights of the estimated age are high and the same age. In various embodiments, the pre-defined condition is: m>3 and m/n>=1/4, wherein m denotes the number of users whose age weights of the estimated age are high and the same age in the classmate relationship data, wherein n denotes a total number of users in the classmate relationship. Since the ages of users in a classmate relationship are usually the same or similar, the ages of the users whose age weights are low or medium are adjusted according to the estimated age of the users whose age weights are high. Thus, the estimated ages are more accurate.

The units as shown in FIG. 5 and FIG. 6 may be implemented by hardware, machine-readable instructions, or a combination of hardware and machine-readable instructions. Machine-readable instructions used in the examples disclosed herein may be stored in a non-transitory storage medium readable by one or more processors, such as hard drive, CD-ROM, DVD, compact disk, floppy disk, magnetic tape drive, RAM, ROM, or any other proper storage device.

A machine-readable storage medium is also provided to store instructions to cause one or more processors to execute a process as described according to the examples herein. In one example, a system or apparatus having a storage medium that stores machine-readable program codes for implementing functions of any of the above examples and that may cause the system or the apparatus (or CPU or MPU) to read and execute the program codes stored in the storage medium is provided.

In this situation, the program codes read from the storage medium may implement any one of the above examples.

The storage medium for storing the program codes may include floppy disk, hard drive, compact disk (such as CD-ROM, CD-R, CD-RW, DVD-ROM, DVD-RAM, DVD-RW, DVD+RW), magnetic tape drive, flash card, and so on. The program codes may also be downloaded from a server computer via a communication network.

What has been described and illustrated herein is a preferred example of the disclosure along with some of its variations. The terms, descriptions and figures used herein are set forth by way of illustration only and are not meant as limitations. Many variations are possible within the spirit and scope of the disclosure, which is intended to be defined by the following claims—and their equivalents—in which all terms are meant in their broadest reasonable sense unless otherwise indicated.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Reference throughout this specification to "one embodiment," "an embodiment," "specific embodiment," or the like in the singular or plural means that one or more particular features, structures, or characteristics described in connection with an embodiment is included in at least one embodiment of the present disclosure. Thus, the appearances of the phrases "in one embodiment" or "in an embodiment," "in a specific embodiment," or the like in the singular or plural in various places throughout this specification are not necessarily all referring to the same embodiment. Furthermore, the particular features, structures, or characteristics may be combined in any suitable manner in one or more embodiments.

What is claimed is:

1. A system for estimating age of a user, comprising:
   memory;
   one or more processors; and
   at least one unit stored in the memory for execution by the one or more processors, the at least one unit comprises:
   a weight configuring unit, to obtain different kinds of basic age data of the user from network products that comprise an instant messaging tool and a Social Networking Service (SNS), wherein the different kinds of basic age data are provided by the user by filling in ages through the different kinds of network products, obtain reference age data of the user through network questionnaire, compare the basic age data with the reference age data to obtain an accuracy ratio of the basic age data; and configure an initial weight for the basic age data according to the accuracy ratio;
   a weight processing unit, to obtain an age weight of the user in each kind of basic age data according to a sum of the initial weight and an age weight score of the kind of basic age data; wherein the age weight score of the kind of basic age data is configured according to the initial weight of the kind of the basic age data and an age similarity of the user in the different kinds of basic age data; and an age estimating unit, to search the different kinds of basic age data for the basic age data with a largest age weight, and estimate the age of the user according to the basic age data with the largest age weight;

wherein the accuracy ratio of the basic age data comprises searching the basic age data for a selected group of users whose ages conform to the reference age data, dividing the number of the users searched out by the total number of users in the basic age data, and determining the divided result as the accuracy ratio of the basic age data.

2. The system of claim 1, wherein the weight configuring unit is further to configure the initial weight for each kind of basic age data according to a source of the basic age data.

3. The system of claim 1, wherein the weight processing unit is further to compare the estimated age of the user with the initial weight, and classify, according to a compared result, the age weight of the estimated age into one of three levels: high weight, medium weight and high weight.

4. The system of claim 1, wherein the age estimating unit is further to obtain an estimated age of the user in classmate relationship data, and adjust estimated ages of other users in the classmate relationship according to the estimated age of the user and the age weight of the user.

5. The system of claim 1, wherein the age estimating unit is further to search classmate relationship data for users whose age weights of estimated age are high and having the same age, determine whether the number of the user searched out meets a pre-defined condition, if the number meets the pre-defined condition, adjust ages of users in the classmate relationship data whose age weights of estimated ages are medium and low to the estimated age of the users whose age weights of the estimated age are high and having the same age.

6. The system of claim 1, further comprising:
an age data storage unit, to store the basic age data and reference age data; and
a classmate relationship data storage unit, to store classmate relationship data.

7. A non-transitory computer readable storage medium storing one or more programs for estimating age of a user based on mass data, the set of instructions to direct at least one processor to perform acts of:
obtaining different kinds of basic age data of the user from network products that include an instant messaging tool and a Social Networking Service (SNS), wherein the different kinds of basic kinds of basic age data are provided by the user by filling in ages through the different kinds of network products, configuring an initial weight for each kind of basic age data according to an accuracy ratio of the basic age data;

obtaining an age weight of the user in each kind of basic age data according to a sum of the initial weight and an age weight score of the kind of basic age data; wherein the age weight score of the kind of basic age data is configured according to the initial weight of the kind of basic age data and an age similarity of the user in different kinds of basic age data; and searching the different kinds of basic age data for the basic age data with a largest age weight, estimating the age of the user according to the basic age data with the largest age weight;

wherein the configuring the initial weight for each kind of basic age data comprises:
obtaining reference age data of the user through a network inquiry,
comparing the basic age data with the reference age data to obtain an accuracy ratio of the basic age data; and
configuring the initial weight for the basic age data according to the accuracy ratio; and wherein the accuracy ratio of the basic age data comprises searching the basic age data for a selected group of users whose ages conform to the reference age data, dividing the number of the users searched out by the total number of users in the basic age data, and determining the divided result as the accuracy ratio of the basic age data.

8. The computer readable storage medium of claim 7, wherein the weight configuring unit is further to configure the initial weight for each kind of basic age data according to a source of the basic age data.

9. The computer readable storage medium of claim 7, further comprising:
comparing the estimated age of the user with the initial weight, and classify, according to a compared result, the age weight of the estimated age into one of three levels: high weight, medium weight and high weight.

10. The computer readable storage medium of claim 7, further comprising:
obtaining an estimated age of the user in classmate relationship data, and adjusting estimated ages of other users in the classmate relationship data according to estimated age of the user and the age weight of the user.

11. The computer readable storage medium of claim 7, further comprising:
searching classmate relationship data for users whose age weights of estimated age are high and having the same age, determining whether the number of the user searched out meets a pre-defined condition, if the number meets the pre-defined condition, adjusting ages of users in the classmate relationship data whose age weights of estimated ages are medium and low to the estimated age of the users whose age weights of the estimated age are high and having the same age.

* * * * *